United States Patent [19]

Yoshida

[11] 4,450,296

[45] May 22, 1984

[54] PROCESS FOR THE PRODUCTION OF ARYLALKANONE AND INTERMEDIATE

[75] Inventor: Takao Yoshida, West Long Branch, N.J.

[73] Assignee: International Flavors & Fragrances Inc., New York, N.Y.

[21] Appl. No.: 231,772

[22] Filed: Feb. 5, 1981

Related U.S. Application Data

[62] Division of Ser. No. 188,563, Sep. 18, 1980, Pat. No. 4,298,542.

[51] Int. Cl.$^3$ ............................................. C07C 45/45
[52] U.S. Cl. ...................... 568/316; 568/323; 568/397
[58] Field of Search ............... 568/397, 407, 319, 323, 568/316

[56] References Cited

FOREIGN PATENT DOCUMENTS 55-130934 10/1980 Japan ..................................... 568/407
1105455 3/1968 United Kingdom ................. 568/397

OTHER PUBLICATIONS

Cahiez et al., Tet. Letters, #35, pp. 3155–3156 (1976).
Khorasch et al., "Grignard Reactions of Nonmetallic Substances", pp. 846–869 (1954).
Tamura et al., Bull. Chem. Soc. Jop., vol. 44, pp. 3063–3073 (1971).
Neuman et al., J. Org. Chem., vol. 13, pp. 592–598 (1948).
Watanabe et al., Chem. Abst., vol. 82, #42943h (1975).

Primary Examiner—James H. Reamer
Attorney, Agent, or Firm—Arthur L. Liberman

[57] ABSTRACT

A process for producing 2-methyl-2-phenyl-4-hexanone comprising reacting the Grignard reagent having the structure:

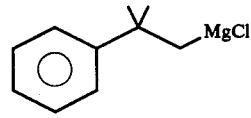

with propianic anhydride having the structure:

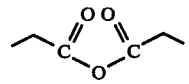

1 Claim, 2 Drawing Figures

GLC PROFILE FOR EXAMPLE I. FRACTIONS 5-10 OF FRACTIONAL DISTILLATION.

PROCESS FOR THE PRODUCTION OF ARYLALKANONE AND INTERMEDIATE

This is a divisional of application for U.S. Letters Patent Ser. No. 188,563 filed on Sept. 18, 1980, now U.S. Pat. No. 4,298,542 issued on Nov. 3, 1981.

BACKGROUND OF THE INVENTION

The compound 2-methyl-2-phenyl-4-hexanone having the structure:

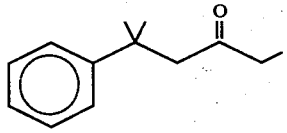

is well known as having an outstanding rose fragrance. Thus, the U.K. Pat. No. 1,105,455 discloses the use of this material in perfumery and further indicates that a process can be use to prepare this material by reacting an acyl chloride with the Grignard reagent having the structure:

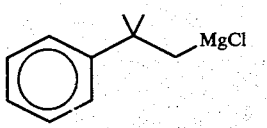

Indeed, United Kingdom patent specification No. 1,105,455 specifically discloses the reaction:

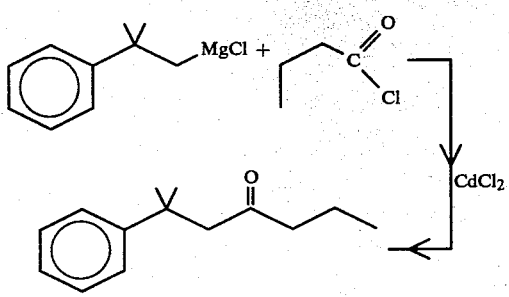

and indicates that such reaction preferably takes place in the precense of cadium chloride. United Kingdom patent specification No. 1,105,455 however, does not actually exemplify such a reaction and further does not alude to the unexpected, unobvious and advantageous increase in yield by carrying out the alternative reaction of our invention using propianic anhydride and the Grignard reagent having the structure:

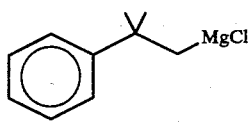

and further does not indicate the advantage from a yield standpoint of first reacting the Grignard reagent having the structure:

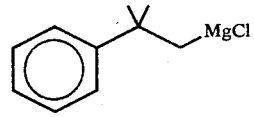

with manganese chloride to form the novel intermediate having the structure:

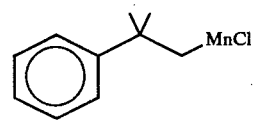

and then reacting the said intermediate having the structure:

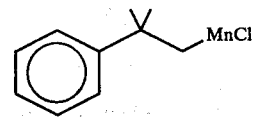

with propionyl chloride having the structure:

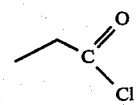

Although the generic reaction of an acyl anhydride with an alkyl magnesium halide to form a ketone is well known in organic chemistry, that is the reaction:

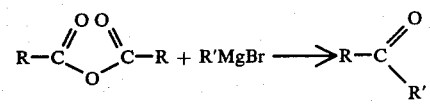

as it is indicated by Newman & Smith at J. Org. Chem. 13, 592-8 (1948) wherein R is methyl and R' may be secondary butyl, tertiary butyl, n-butyl or phenyl, the reaction of a sterically hindered Grignard reagent with an acyl anhydride or the unexpected, advantageous improvement in yield by first forming the mangenese organometallic intermediate from the Grignard reagent and then reacting it with an acyl chloride is not so taught in the prior art.

DETAILED DESCRIPTION OF THE DRAWINGS

Figure 1:
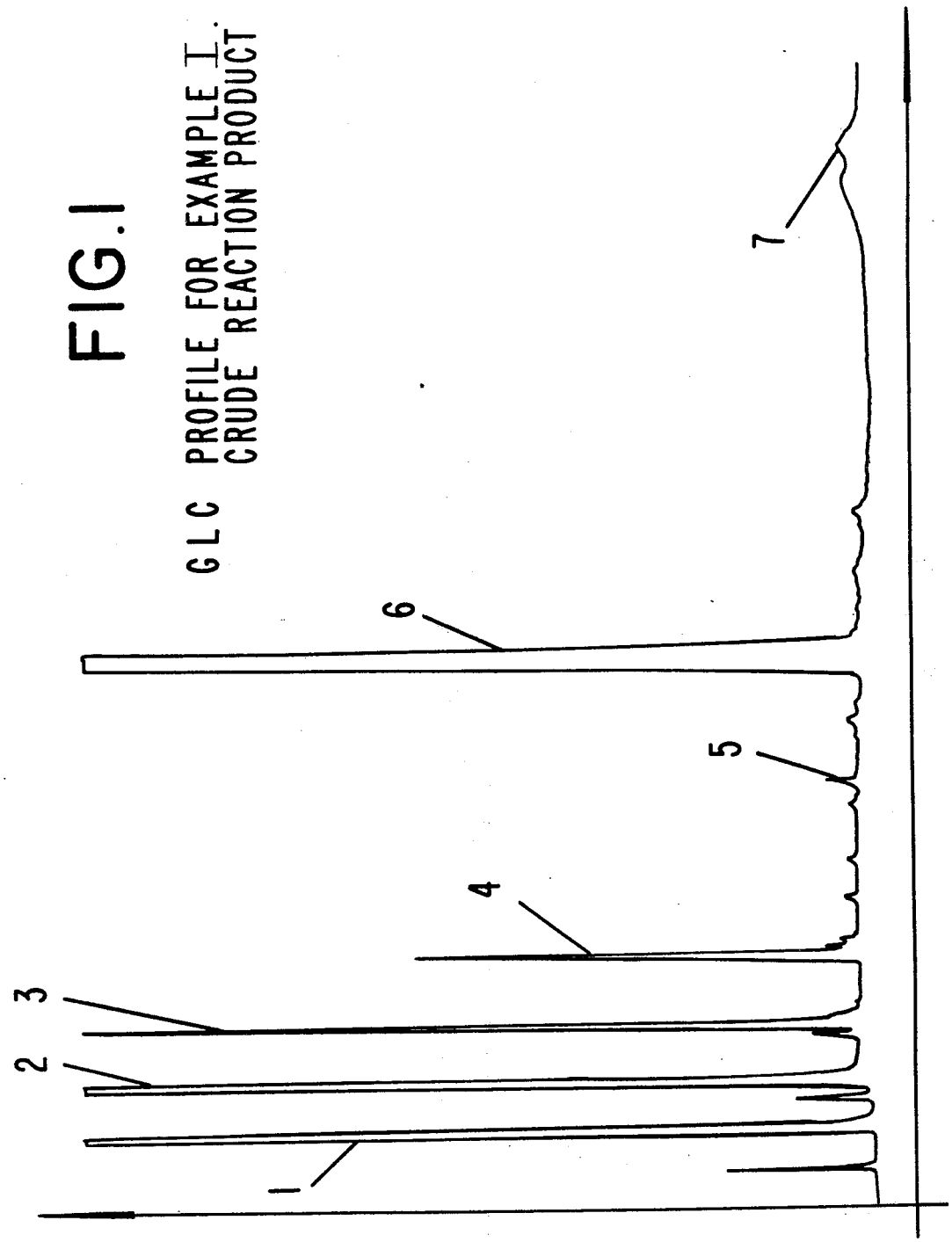
FIG. 1 sets forth the GLC profile for the reaction product (crude prior to distillation) of Example I.

In FIG. 1, the GLC profile is attained by passing the reaction product through a 10% SE-30, 10 foot × ⅛ inch GLC column programmed at 100° C. up to 220° C. at 10° C. per minute.

Peak 1 is the peak for the tetrahydrofuran solvent, tetrahydrofuran having the structure:

Peak 2 is the peak representing the toluene solvent.

Peak 3 is the peak representing the solvent for propionic anhydride reactant having the structure:

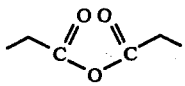

Peak 4 is the peak representing t-butyl benzene having the structure:

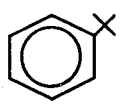

Peak 5 is the peak representing "neophyl" chloride having the structure:

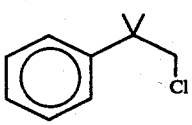

which is 2-methyl-2-phenyl-1-chloropropane.

Peak 6 is the peak representing the reaction product 2-methyl-2-phenyl-4-hexanone having the structure:

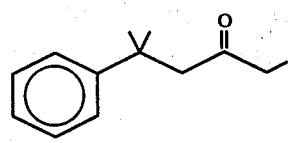

Peak 7, in FIG. 1, represents the dimerization product having the structure:

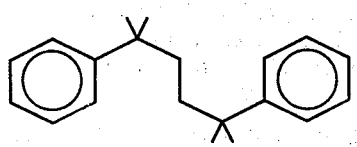

Figure 2:
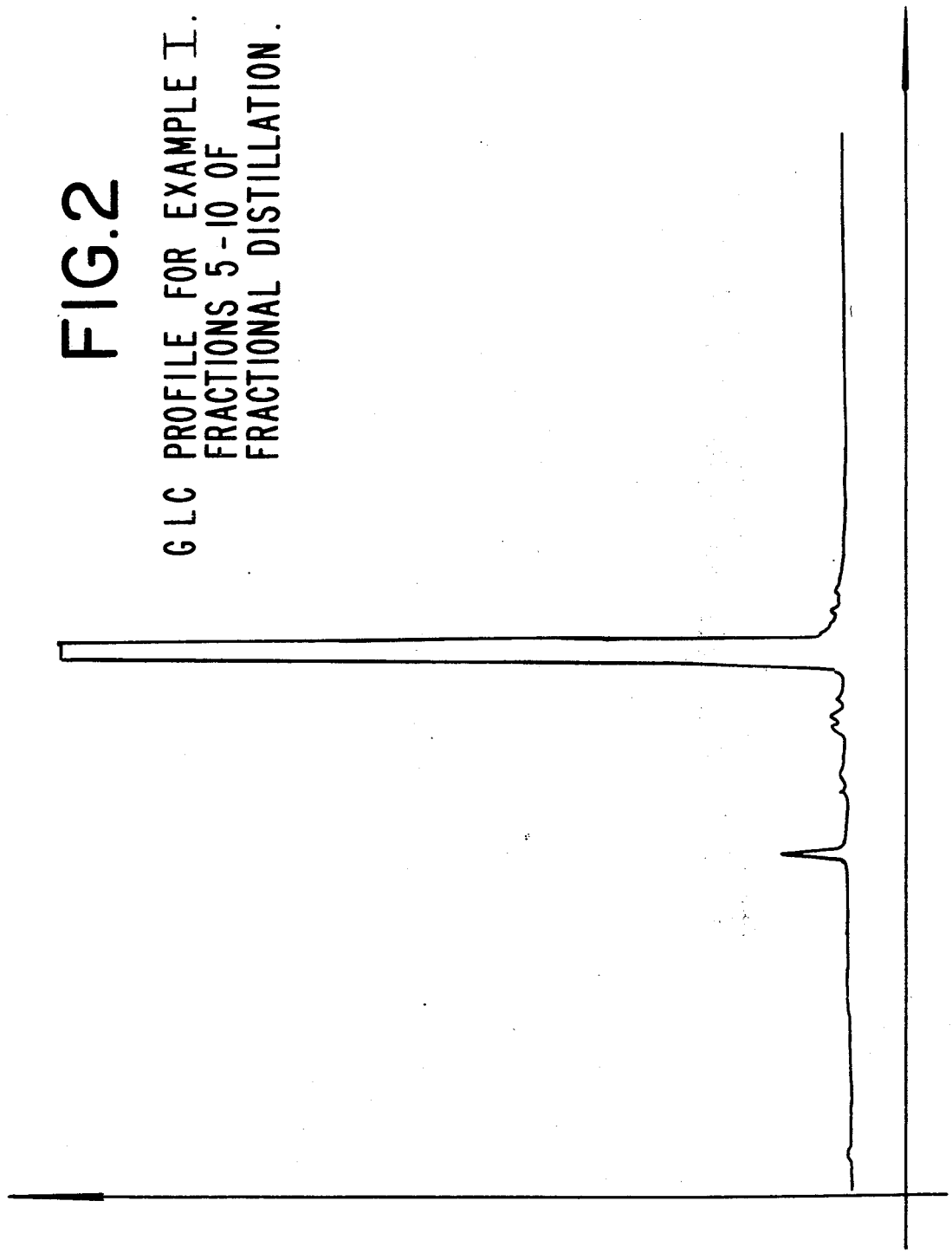
FIG. 2 sets forth the GLC profile for fractions 5-10 of the fractional distillation product of the reaction product of Example I.

In FIG. 2, the peak designated by the number 8 is 2-methyl-2-phenyl-4-hexanone having the structure:

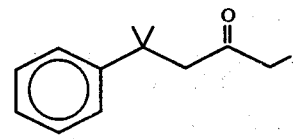

The conditions for producing the GLC profile of FIG. 2 are identical to those conditions used in producing the GLC profile for FIG. 1.

THE INVENTION

The present invention provides a simple economic and efficient process for producing 2-methyl-2-phenyl-4-hexanone having the structure:

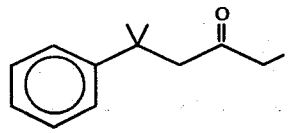

as well as intermediates for preparing same. The process of my invention involves carrying out the reaction of "neophyl chloride Grignard reagent" having the structure:

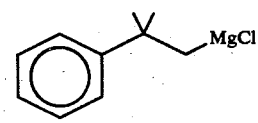

with either propionic anhydride having the structure:

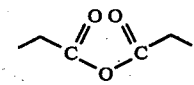

or with manganese chloride to form the compound:

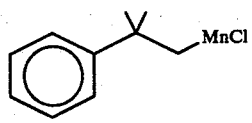

followed by reaction with propionyl chloride having the structure:

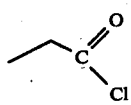

to form the compound having the structure:

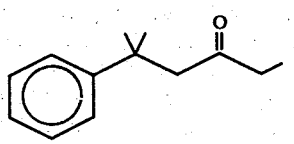

2-methyl-2-phenyl-4-hexanone.

In the reaction of the Grignard having the structure:

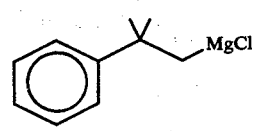

with propionic anhydride having the structure:

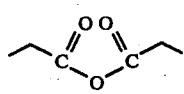

the reaction sequence is as follows:

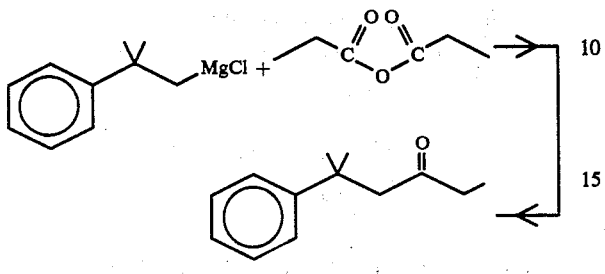

in this reaction, the addition mode may be one of two alternative modes; (i) addition of the propionic anhydride to the Grignard reagent or (ii) addition of the Grignard reagent to the propionic anhydride or mixture of propionic anhydride and cuprous chloride ($Cu_2Cl_2$, used as a catalyst). The reaction may take place in the presence of a cuprous chloride catalyst or in the absence of such cuprous chloride catalyst. The mole ratio of propionic anhydride:Grignard reagent having the structure:

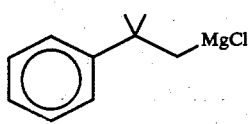

may vary from 0.5:1 up to about 2:1 with a preferred mole ratio range of propionic anhydride:Grignard reagent being from 0.9:1 up to 1.3:1. The temperature of reaction may vary from −23° C. up to 10° C. with a temperature of reaction of −10° C. up to 0° C. being preferred. When using a cuprous chloride catalyst, the mole ratio of cuprous chloride:Grignard reagent may vary from 1:10 up to 1:1 with a mole ratio range of cuprous chloride:Grignard reagent of 1:8 up to 1:2 being preferred.

The reaction may be carried out in the presence of a solvent which is inert to the reaction ingredients such as tetrahydrofuran, toluene and diethyl ether or mixtures of same. The most preferred solvent is a mixture of tetrahydrofuran and toluene. The concentration in moles per liter of solvent may vary from about 1 up to about 5 moles of propionic anhydride per liter of solvent with a preferred concentration of propionic anhydride per liter of solvent being from 2 up to 3 moles of propionic anhydride per liter of solvent. When using a mixture of tetrahydrofuran and toluene as the solvent, the volume/volume ratio of toluene:tetrahydrofuran may vary from 0.1:1 up to 1:0.1 with a preferred volume/volume ratio of toluene:tetrahydrofuran being from 1:1 up to 3:1.

The time of reaction is measured insofar as the time of addition of reactants is concerned and time of ageing of reaction mass after the addition. Thus, the time of addition of reactants may vary from 0.5 hours up to 4 hours and the time of ageing may vary from 0.5 up to 4 hours. Longer times of reaction give rise to an increase in the overall yield of reaction product but most of the yield of reaction product is realized after one hour of ageing.

In carrying out the reaction sequence:

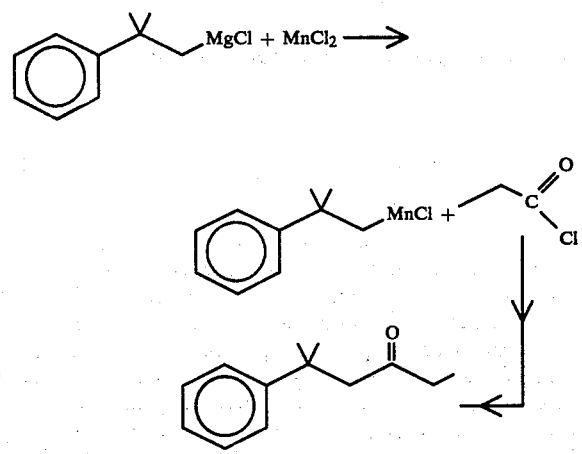

the mole ratio of $MnCl_2$:Grignard reagent having the structure:

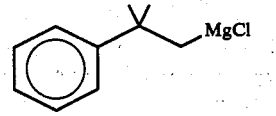

is about 1:1.

The mole ratio of propionyl chloride having the structure:

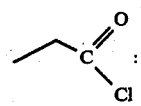

organometallic manganese compound having the structure:

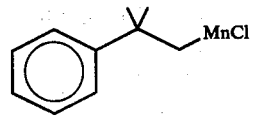

is about 1.1:1.

The temperature of reaction for the reaction of the Grignard reagent having the structure:

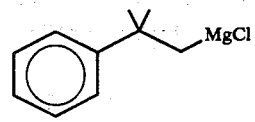

with $MnCl_2$ may vary from about 0° C. up to 30° C. and the temperature of reaction for the reaction of the organometallic compound having the structure:

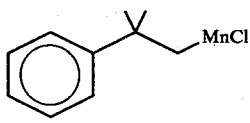

with the propionyl chloride having the structure:

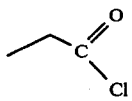

may vary from about 30° C. up to about 50° C. A solvent should be used in this reaction which is inert to the reaction ingredients and the most preferred solvent is diethyl ether. The reaction pressure may vary from 1 up to 2 atmospheres depending upon the desired temperature of reaction and solvent used. Refluxed temperatures are preferred and accordingly, appropriate pressures are to be employed. The time of reaction is a function of time of addition and time of ageing. The time of addition may vary from 0.5 up to 3 hours and the time of ageing may vary from 1 up to 8 hours. The molar concentration of reactant in solvent may vary from 2 moles Grignard reagent per liter of solvent used up to about 5 moles of Grignard reagent per liter of solvent used.

In general precedent in the prior art exists for a reaction to make such a sterically hindered compound such as the compound having the structure:

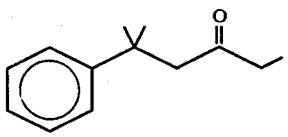

using the Grignard reagent having the structure:

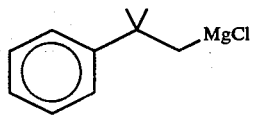

and propionic anhydride having the structure:

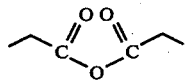

particularly in the absence of a catalyst. The steric hindrence of the starting Grignard reagent gives rise to an expectation of very low, if not negligible yield. However, as will be noted by a comparison of Table 1 (set forth in Example I) and Table 2 (set forth in Example II) the yields of reaction product having the structure:

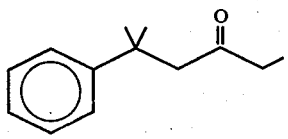

are far greater using propionic anhydride than when using the propionyl chloride having the structure:

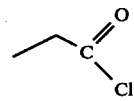

even when using the manganese chloride reaction product of the Grignard reagent having the structure:

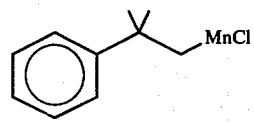

to react with propionyl chloride having the structure:

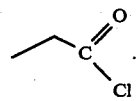

The following examples are given to illustrate embodiments of my invention as it is presently preferred to practice it. It will be understood that these examples are illustrative and the invention is not to be considered as restricted thereto, except as indicated in the appended claims. Certain examples set forth in Table 2 of Example II are illustrative of the prior art.

EXAMPLE I

PREPARATION OF 2-METHYL-2-PHENYL-4-HEXANONE

Reaction:

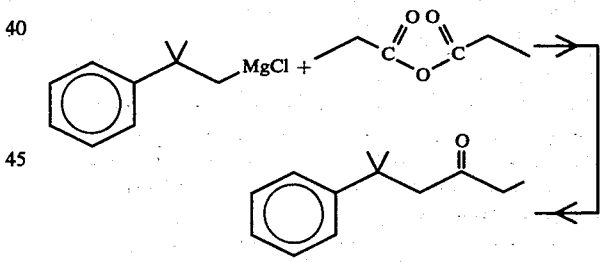

Equipment:
5 liter and 12 liter three neck reaction flasks;
Reflux condenser;
Addition funnel;
Y-adapter;
Thermomether;
Bubbler;
Stirrer.
Reagents:
Neophyl chloride, having the structure:

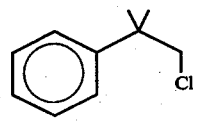

1348 g (8 moles);

Magnesium 192 g (8 moles);
Propionic anhydride 1248 g (9.6 moles);
Toluene 2100 ml;
Tetrahydrofuran anhydrous 800 ml;
Acetic acid 2000 g.

Procedure:

1. Tetrahydrofuran (800 ml) and magnesium (192 g) are placed in a 5-liter three neck reaction flask equipped with a reflux condenser, a thermometer, an addition funnel and a stirrer. The system is purged with nitrogen to replace air in the system and the static nitrogen blanket is placed throughout the reaction.
2. The resulting mixture is then heated to 65° C.
3. Neophyl chlolride (25 g) is added at 65° C. to start the reaction (see Note 1).
4. After the reaction is commenced, a mixture of neophyl chloride (1323 g) and toluene (1600 ml) is added at 55° C.–65° C. over a period of 90 minutes.
5. The reaction mixture is stirred at 60° C. for additional 4 hours and then cooled to room temperature (about 25° C.).
6. Toluene (500 ml), THF (1200 ml) and propionic anhydride are placed in a 12-liter three neck reaction flask fitted with a reflux condenser, a thermometer, an addition funnel and a stirrer. The system is flushed with nitrogen to replace air in the system and the static nitrogen blanket is placed throughout the reaction over the reaction mass.
7. The mixture is cooled to −10° C. (see Note 3).
8. The Grignard reagent solution prepared in step 5 is placed in the addition funnel (see Note 4) and is added to the solution at −10° C. up to about 0° C. over a period of 5 hours (see Notes 3 and 5).
9. The reaction mixture is stirred at 0° C.–25° C. for for an additional 2 hours. The GLC profile of the reaction product at the end of this two-hour period is set forth in FIG. 1, (see Note 6).
10. The reaction mass is poured into 50% aqueous acetic acid solution (4000 ml) at 25° C.–35° C. (In view of the high exothermicity of the reaction the mixture is poured very slowly). The mixture is then stirred for 30 minutes (see Note 7).
11. The organic layer is separated and washed with saturated sodium bicarbonate solution (1000 ml) until the pH value of the aqueous layer becomes 7–8; and then with a saturated sodium chloride solution (1000 ml). The organic layer weighs 3940 g.
12. The organic layer is distilled on a one-plate ½ inch splash column with 50 g of Primol ® and 0.1 g of Ionox ® to yield the following fractions:

| Fraction No. | Vapor Temp. (°C.) | Liquid Temp. (°C.) | Vacuum (mm Hg) | Weight (g.) | Product[a] (g.) |
|---|---|---|---|---|---|
| 1 | 32–60 | 41–100 | 100–125 | 2231 | (lites) |
| 2 | 65–166 | 93–210 | 3 | 1577 | 1257 | the residue weighs 28 g.
([a]by GLC analysis: 10% SE 30 column, 10′ × ⅛′, programmed at 100°–220° C., at 10° C./min.)

13. Fraction 2 is then fractionated under 3 mmHg pressure at 2:1 reflux ratio using a 18″×1″ goodloe packed column and 50 g of Promol ® and 0.1 g of Ionox ® to give the following fractions:

| Fraction No. | Vapor Temp. (°C.) | Liquid Temp. (°C.) | Weight (g) | Product[a] (g) |
|---|---|---|---|---|
| 1, 2 | 49–79 | 109–115 | 133 | Lites |
| 3 | 79–91 | 115–118 | 86 | 1 |
| 4 | 91–100 | 118 | 119 | 73 |
| 5–10 | 100–108 | 118–156 | 1140 | 1122 |
| 11 | 108–110 | 156–205 | 27 | 25 |

The residue weighs 36 g.
(Note [a]By GLC analysis, 10% SE-30 column 10′ × ⅛″, programmed at 100° C.–220° C. at 10° C./minute.

Chemical yield:
1221 g (80% of theory based on neophyl chloride charged)

Using the procedure of this Example, the following runs (Example IB) 1–9 are carried out. In certain cases a catalyst, cuprous chloride, $Cu_2Cl_2$ is used. In certain cases a solvent, diethyl ether is used in place of the tetrahydrofuran-toluene mixture. The amount of diethyl ether used is equal to the amount of tetrahydrofuran-toluene mixture.

TABLE 1
(Example IB)
(REACTION OF NEOPHYLMAGNESIUM CHLORIDE AND PROPIONIC ANHYDRIDE)

| | REAGENT MOLE | | | | REACTION | | | | | |
|---|---|---|---|---|---|---|---|---|---|---|
| | Grignard reagent | | | | Addition | | Aging | | | |
| Run | (neophylmagnesium chloride) | Propionic anhydride | $Cu_2Cl_2$ catalyst | Solvent | Temp. | Time (hr) | Temp. | Time (hr) | Addition[d] mode | Yield (%) |
| 1 | 0.25 | 0.30 | 0.25 | diethyl ether | −10° C.–0° C. | 1.5 | −10° C.–0° C. | 0.5 | B | 60[a] |
| 2 | 0.25 | 0.30 | 0.125 | diethyl ether | −10° C. | 2.5 | −10° C.–0° C. | 2.0 | B | 67[a] |
| 3 | 2.00 | 2.40 | 1.00 | diethyl ether | −10° C.–0° C. | 2.5 | −10° C.–0° C. | 3.0 | B | 63[c] |
| 4 | 1.00 | 1.20 | 0.50 | THF—Toluene | −10° C.–0° C. | 1.5 | 0° C. | 3.0 | B | 72[b] |
| 5 | 1.00 | 0.94 | 0.25 | THF—Toluene | −10° C.–0° C. | 0.6 | −10° C.–0° C. | 3.0 | B | 80[b] |
| 6 | 1.00 | 0.94 | 0.125 | THF—Toluene | −10° C.–0° C. | 3.0 | −10° C.–0° C. | 3.0 | B | 74[b] |
| 7 | 0.50 | 0.47 | — | THF—Toluene | −10° C.–0° C. | 0.5 | −10° C.–0° C. | 2.0 | B | 77[a] |
| 8 | 8.00 | 9.60 | — | THF—Toluene | −10° C.–0° C. | 2.0 | −10° C.–0° C. | 5.0 | B | 80[c] |
| 9 | 1.60 | 1.92 | — | THF—Toluene | 0° C. | 1.0 | 0° C.–20° C. | 2.0 | A | 63[b] |

NOTES:
[a]Calculated by GLC analysis on the reaction mixture.
[b]Calculated by GLC analysis on the rushed over materials (distillation on a one-plate column).
[c]Calculated by GLC analysis on the fractionated materials.
[d]Addition mode:
A - Addition of propionic anhydride to the Grignard reagent.
B - Addition of the Grignard reagent to the mixture of propionic anhydride and $Cu_2Cl_2$.

EXAMPLE II

PREPARATION OF
2-METHYL-2-PHENYLHEXENOL

Reaction:

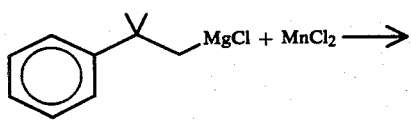

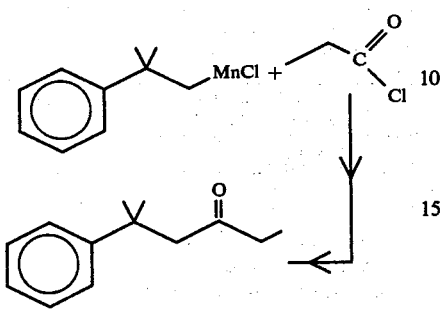

Into a one liter three-neck reaction flask equipped with thermometer, reflux condenser and addition funnel is placed 12 g (0.5 moles) of magnesium and 200 ml diethyl ether. Separately, a solution of 85 g (0.5 moles) of neophyl chloride in 100 ml diethyl ether is prepared. 10% of neophyl chloride solution is then added to the magnesium/diethyl ether mixture. The reaction formed from Grignard reagent is commenced using iodine crystals and a small amount of Vitride ®. After the reaction has commenced the remaining neophyl chloride solution is added over a period of two hours at gentle reflux. After the addition of the neophyl chloride, the reaction mass is refluxed for one hour. The reaction mass is then cooled to −10° C. and 63 g of manganese chloride (MnCl₂) is added slowly in small portions. The reaction mass is then stirred for a period of 2 hours at −10° C.−0° C. Over a period of 30 minutes, 51 g of propionyl chloride is added to reaction mass while maintaining it at 0° C. The reaction mass is allowed then to exotherm to 50° C. and the diethyl ether solvent is permitted to evaporate.

300 cc of 10% acetic acid is then added to the reaction mass at 10° C. The reaction mass is then poured into a separatory funnel and is washed with saturated sodium carbonate to a pH of 7 followed by three two 200 ml portions of sodium chloride.

The reaction mass is dried over anhydrous sodium sulfate, filtered and stripped of solvent to yield a product weighing 77 g.

This material is distilled at 108° C. and 3 mmHg pressure. MNR, IR and mass spectral analysis confirm that the product has the structure:

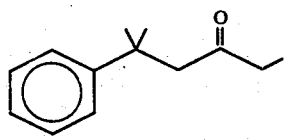

The following table sets forth runs 1-12 utilizing a procedure identical to the procedure of the foregoing example. In place of using diethyl ether and equal volume of tetrahydrofuran/toluene mixture (5050 volume/volume) is used. The mode of addition of reactants is varied from (i) addition of $MX_n$ (e.g. manganese chloride) to the Grignard reagent followed by addition of propionyl chloride or (ii) addition of the Grignard reagent to the mixture of propionyl chloride and $MX_n$ (e.g. manganese chloride).

TABLE 2
(EXAMPLE IIB)
(REACTION OF NEOPHYLMAGNESIUM CHLORIDE AND PROPIONYL CHLORIDE)

| | REAGENT MOLE | | | | REACTION | | | | | |
|---|---|---|---|---|---|---|---|---|---|---|
| | Grignard reagent | | | | Addition | | Aging | | | |
| Run | (neophylmagnesium chloride) | Propionyl chloride | $MX_n$ | Solvent | Temp. | Time (hr) | Temp. | Time (hr) | Addition[c] mode | Yield (%) |
| 1 | 1.0 | 1.0 | — | THF—Toluene | 0° C. | 1.5 | 0° C. | 2 | B | 23[b] |
| 2 | 2.0 | 2.2 | MnCl₂ (2.0) | THF—Toluene | −10° C.−35° C. | 1.0 | 20° C.−35° C. | 1 | A | <5[a] |
| 3 | 2.0 | 2.2 | MnCl₂ (0.2) | THF—Toluene | −10° C.−23° C. | 2.5 | −10° C.−20° C. | 2 | A | <5[a] |
| 4 | 2.0 | 2.2 | MnCl₂ (0.2) | THF—Toluene | 0° C. | 2.0 | 0° C. | 2 | B | 36[b] |
| 5 | 1.0 | 1.0 | MnCl₂ (1.1) | THF—Toluene | 0° C. | 1.0 | 0° C.−34° C. | 4 | B | 38[b] |
| 6 | 0.5 | 0.55 | MnCl₂ (0.5) | diethyl ether | 0° C. | 0.5 | 0° C.−50° C. | 1 | A | 39[a] |
| 7 | 0.5 | 0.55 | MnCl₂ (0.5) | diethyl ether | 0° C. | 0.5 | 10° C. | 2 | A | 4[a] |
| 8 | 0.05 | 0.05 | MnCl₂ (0.005) | diethyl ether | 0° C. | 0.1 | 0° C. | 4 | B | 16[a] |
| 9 | 1.0 | 1.0 | ZnCl₂ (1.0) | THF—Toluene | 0° C. | 0.5 | 0° C. | 8 | B | 12[a] |
| 10 | 0.05 | 0.05 | NiBr₂ (0.005) | THF—Toluene | 0° C.−5° C. | 0.5 | 0° C. | 4 | B | 36[a] |
| 11 | 0.5 | 0.55 | Cu₂Cl₂ (0.25) | THF—Toluene | −10° C. | 0.5 | −10° C.−20° C. | 15 | A | 30[a] |
| 12 | 0.5 | 0.5 | Cu₂Cl₂ (0.25) | THF—Toluene | 0° C. | 1.0 | 0° C.−25° C. | 4 | B | 48[a] |

NOTES:
[a] Calculated by GLC analysis on the reaction mixture.
[b] Calculated by GLC analysis on the rushed over materials (distilled on a one-plate column).
[c] Addition mode:
A - Addition of $MX_n$ to the Grignard reagent followed by addition of propionyl chloride.
B - Addition of the Grignard reagent to the mixture of propionyl chloride and $MX_n$

What is claimed is:
1. A process for preparing 2-methyl-2-phenyl-4-hexanone having the structure:

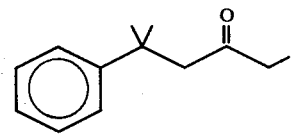

comprising the step of intimately admixing propionic anhydride having the structure:

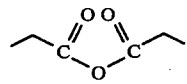

with neophymagnesium chloride having the structure:

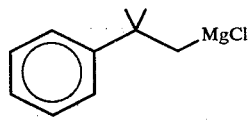

in the presence of an inert solvent selected from the group consisting of diethylether, toluene and tetrahydrufuran, the reaction taking place in the presence of or in the absence of a cuprous chloride catalyst; the mole ratio of propionic anhydride:neophylmagnesium chloride being from 0.5:1 up to about 2:1; the temperature of reaction being from −10° C. up to 0° C.; the concentration of propionic anhydride in solvent being from about 1 up to about 5 moles of propionic anhydride per liter of solvent; the time of addition of one reactant to the other varying from 0.5 hours up to 4 hours and the time of aging of the reaction mass being from 0.5 up to 4 hours.

* * * * *